US008101792B2

(12) United States Patent  
Sheu et al.

(10) Patent No.: US 8,101,792 B2  
(45) Date of Patent: Jan. 24, 2012

(54) **COMPOUNDS ISOLATED FROM *ANTRODIA CINNAMOMEA* AND USE THEREOF**

(75) Inventors: Chia-Chin Sheu, Taoyuan County (TW); Masao Hattori, Toyama (JP)

(73) Assignee: Simpson Biotech Co., Ltd., Taoyuan County (TW)

( * ) Notice: Subject to any disclaimer, the term of this patent is extended or adjusted under 35 U.S.C. 154(b) by 0 days.

(21) Appl. No.: 12/678,612

(22) PCT Filed: Sep. 17, 2007

(86) PCT No.: PCT/CN2007/002727
§ 371 (c)(1),
(2), (4) Date: Mar. 17, 2010

(87) PCT Pub. No.: WO2009/036590
PCT Pub. Date: Mar. 26, 2009

(65) Prior Publication Data
US 2010/0210865 A1 Aug. 19, 2010

(51) Int. Cl.
*C07C 69/76* (2006.01)
(52) U.S. Cl. .................................... 560/55
(58) Field of Classification Search .......... None
See application file for complete search history.

(56) References Cited

OTHER PUBLICATIONS

Schlogl et al. (Monatshefte fuer Chemie, 1961, 92, 51-71).*
STN abstract of Schlogl et al. (Monatshefte fuer Chemie, 1961, 92, 51-71) Accession No. 1961:118312.*
English Translation of Schlogl et al. (Monatshefte fuer Chemie, 1961, 92, 51-71).*
Tsai ZT, Treatment of Acute Viral Hepatitis, Chronic Viral Hepatitis and Cirrhosis by *Ganoderma lucidum*, 1982, pp. 160-171, Sheng-Yun Publisher, Inc.
Chung-Hsiung Chen et al., New Steroid Acids from *Antrodia cinnamomea*, a Fungal Parasite of *Cinnamomum micranthum*, Journal of Natural Products, Nov. 1995, pp. 1655-1661, vol. 58, No. 11.
Shu-Wei Yang et al., Steroids and Triterpenoids of *Antrodia cinnamomea*—A Fungus Parasitic on *Cinnamomum micranthum*, Phytochemistry, 1996, pp. 1389-1392, vol. 41, No. 5, Great Britain.
I-Hwa Cherng et al., Three New Triterpenoids from *Antrodia cinnamomea*, Journal of Natural Products, Mar. 1995, pp. 365-371, vol. 58, No. 3.
I-Hwa Cherng et al., Triterpenoids from *Antrodia cinnamomea*, Phytochemistry, 1996, pp. 263-267, vol. 41, No. 1, Great Britain.
Cheng-Chi Chen et al., Neuroprotective Diterpenes from the Fruiting Body of *Antrodia camphorata*, Journal of Natural Products, 2006, pp. 689-691, vol. 69, No. 4.
Hung-Chen Chiang et al., A Sesquiterpene Lactone, Phenyl and Biphenyl Compounds from *Antrodia cinnamomea*, Phytochemistry, 1995, pp. 613-616, vol. 39, No. 3, Great Britain.
Keh-Feng Huang et al., Phenyl Compounds from *Antrodia cinnamomea*, The Chinese Pharmaceutical Journal, 2001, pp. 327-331, vol. 53, No. 6.
George Hsiao et al., Antioxidative and Hepatoprotective Effects of *Antrodia camphorata* Extract, Journal of Agricultural and Food Chemistry, 2003, pp. 3302-3308, vol. 51, No. 11.

(Continued)

*Primary Examiner* — Daniel Sullivan
*Assistant Examiner* — Jennifer C Sawyer
(74) *Attorney, Agent, or Firm* — WPAT, P.C.; Anthony King

(57) ABSTRACT

The present invention relates to novel compounds from *Antrodia cinnamomea* and their use.

9 Claims, 8 Drawing Sheets

OTHER PUBLICATIONS

Tuzz-Ying Song et al., Protective Effects of Fermented Filtrate from *Antrodia camphorata* in Submerged Culture against CCl4-Induced Hepatic Toxicity in Rats, Journal of Agricultural and Food Chemistry, 2003, pp. 1571-1577, vol. 51, No. 6.

Hao-Feng Han et al., Protective Effects of a Neutral Polysaccharide Isolated from the Mycelium of *Antrodia cinnamomea* on Propionibacterium Acnes and Lipopolysaccharide Induced Hepatic Injury in Mice, 2006, pp. 496-500, vol. 54, No. 4.

Yuh-Chiang Shen et al., Evaluation of the Anti-Inflammatory Activity of Zhankuic Acids Isolated from the Fruiting Bodies of *Antrodia camphorata*, Planta Medica, 2004, pp. 310-314, vol. 70.

You-Cheng Hseu et al., Anti-Inflammatory Potential of *Antrodia camphorata* through Inhibition of iNOS, COX-2 and Cytokines via the NF-KB Pathway, International Immunopharmacology, 2005, pp. 1914-1925, vol. 5.

I-Hung Lee et al., *Antrodia camphorata* Polysaccharides Exhibit Anti-Hepatitis B Virus Effects, Fems Microbiology Letters, 2002, pp. 63-67, vol. 209.

Guei-Jane Wang et al., The Vasorelaxation of *Antrodia camphorata* Mycelia: Involvement of Endothelial CA2+-NO-cGMP Pathway, Life Sciences, 2003, pp. 2769-2783, vol. 73.

Tuzz-Ying Song et al., Mycelia from *Antrodia camphorata* in Submerged Culture Induce Apoptosis of Human Hepatoma HepG2 Cells Possibly through Regulation of Fas Pathway, Journal of Agricultural and Food Chemistry, 2005, pp. 5559-5564, vol. 53, No. 14.

Norio Nakamura et al., Five New Maleic and Succinic Acid Derivatives from the Mycelium of *Antrodia camphorata* and Their Cytotoxic Effects on LLC Tumor Cell Line, Journal of Natural Products, 2004, pp. 46-48, vol. 67, No. 1.

\* cited by examiner

COMPOUNDS ISOLATED FROM *ANTRODIA CINNAMOMEA* AND USE THEREOF

FIELD OF THE INVENTION

The present invention is related to a compound from the metabolite of Antrodin C isolated form *Antrodia cinnamomea*.

BACKGROUND OF THE INVENTION

*Antrodia cinnamomea* (Polyporaceae, Aphyllophorales) is well known in Taiwan as a traditional Chinese medicine. It grows only on the inner heartwood wall of the endemic evergreen *Cinnamomun kanehirai* (Hey)(Lauraceae) in Taiwan. It has been used as treating food to remedy toxication, diarrhea, abdominal pain, hypertension, itchy skin, and liver cancer (Tsai Z T, et al. 1982 *Sheng-Yun Publisher Inc.: Taichung, Taiwan*, pp 116-117). The compounds of steroid acid (Chen C H, et al. 1995 *J Nat Prod* 58: 1655-1661; Yang S W, et al. 1996 *Phytochemistry* 41: 1389-1392), triterpenoids (Cherng I H, et al, 1995 *J Nat Prod* 58: 365-371; Cherng I W, et al. 1996 *Phytochemistry* 41: 263-267), diterpenes (Chen C C, et al. 2006 *J Nat Prod* 69: 689-691), sesquiterpene lactone (Chiang H C, et al. 1995 *Phytochemistry*, 39, 613-616) and phenyl and biphenyl (Chiang H C, et al. 1995 *Phytochemistry*, 39, 613-616; Huang K F, et al. 2001 *Chin Pherm J* 53: 327-331) were isolated from the fruiting body of *Antrodia cinnamomea*, possessing cytotoxic, neuroprotective, anti-inflammatory, apoptotic activities. Moreover, mycelium, another part of *Antrodia cinnamomea* has antioxidative (Hsiao G., et al. 2003 *J Agric Food Chem* 51: 3302-3308; Song T Y, et al. 2003 *J Agric Food Chem* 51: 1571-1577), hepatoprotective (Han H F, et al. 2006 *Chem Pharm Bull* 54: 496-500), anti-inflammatory (Shen Y C, et al. 2004 *Planta Medica* 70: 310-314; Hseu Y C, et al. 2005 *Int Immunopharmacol* 5: 1914-1925), anti-hepatitis B virus (Lee I H, et al. 2002 *FEMS Microbiol Lett* 209: 63-67), vasorelaxation (Wang G. J, et al. 2003 *Life Sci* 73: 2769-2783) and apoptosis (Song T Y, et al. 2005 *J Agric Food Chem* 53: 5559-5564) actions.

SUMMARY OF INVENTION

The present invention provide a compound having the formula

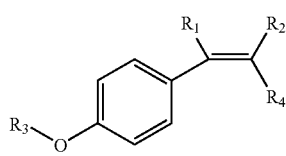

wherein $R_1$ is $C_{1-10}$ carboxylic acid or $C_{1-10}$ ester; $R_2$ is $C_{1-10}$ carboxylic acid or $C_{1-10}$ ester; $R_3$ is H, $C_{1-10}$ alkyl, $C_{2-10}$ alkenyl or $C_{2-10}$ alkynyl; and $R_4$ is H, $C_{1-10}$ alkyl, $C_{2-10}$ alkenyl or $C_{2-10}$ alkynyl.

The present invention also provides a composition comprising a compound having the formula

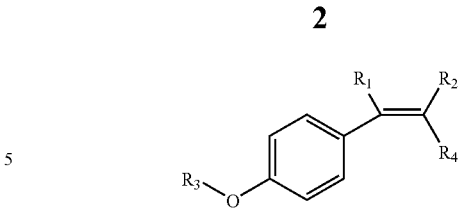

wherein $R_1$ is $C_{1-10}$ carboxylic acid or $C_{1-10}$ ester; $R_2$ is $C_{1-10}$ carboxylic acid or $C_{1-10}$ ester; $R_3$ is H, $C_{1-10}$ alkyl, $C_{2-10}$ alkenyl or $C_{2-10}$ alkynyl; and $R_4$ is H, $C_{1-10}$ alkyl, $C_{2-10}$ alkenyl or $C_{2-10}$ alkynyl.

DETAIL DESCRIPTION OF THE INVENTION

Figure 1:
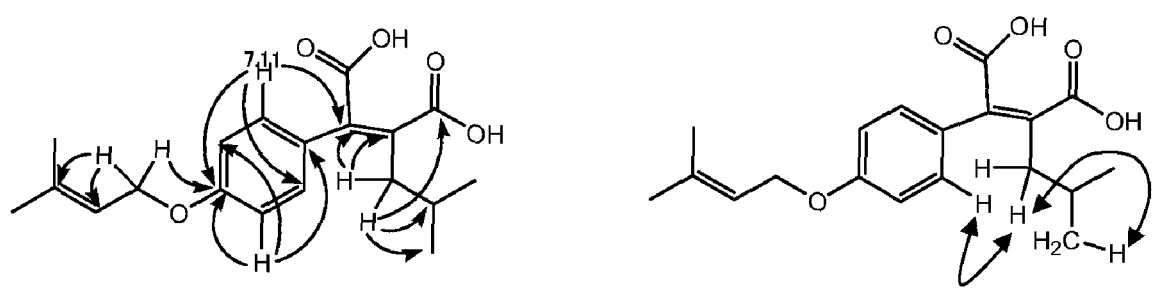
FIG. 1 HMBC (a) and NOE (b) Correlations of M1.

In this invention, three maleic acid and two succinic acid derivatives (Antrodin A-E) were firstly isolated from the mycelium of *Antrodia cinnamomea*, and the cytotoxic activity against LLC cells of Antrodin C and B were confirmed (Nakamura N, et al. 2004 *J Nat Prod* 7: 46-48). Furthermore, Antrodin C, with the highest amounts in mycelium, exhibited protective effect against hepatitis model induced by LPS. Whereas the metabolism study on the compounds of *Antrodia cinnamomea* were never reported. In the present invention, the metabolites of Antrodin C in the rat bile and feces samples were identified by LC/MS-MS with electrospary ionization (ESI), and the pharmacokinetics of M1 in rat bile was performed after oral administration (50 mg/kg) and intravenous injection (10 mg/kg) of Antrodin C by PAD-HPLC.

The present invention provides a compound having the formula

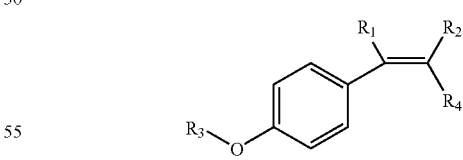

wherein $R_1$ is $C_{1-10}$ carboxylic acid or $C_{1-10}$ ester; $R_2$ is $C_{1-10}$ carboxylic acid or $C_{1-10}$ ester; $R_3$ is H, $C_{1-10}$ alkyl, $C_{2-10}$ alkenyl or $C_{2-10}$ alkynyl; and $R_4$ is H, $C_{1-10}$ alkyl, $C_{2-10}$ alkenyl or $C_{2-10}$ alkynyl.

$R_1$ or $R_2$ of the compound is $C_{1-6}$ carboxylic acid. In the preferred embodiment, $R_1$ or $R_2$ is COOH, $R_3$ is $C_{1-6}$ alkyl and $R_4$ is isobutyl. In the more preferred embodiment, the compound is (2Z)-2-isobutyl-3-{4-[(3-methylbut-2-en-1-yl)oxy]phenyl}but-2-enedioic acid, (2Z)-2-isobutyl-3-{4-[(3-methylbut-2-en-1-yl)oxy]phenyl}but-2-enedioic acid 4-methyl ester or (2Z)-2-isobutyl-3-{4-[(3-methylbut-2-en-1-yl)oxy]phenyl}but-2-enedioic acid 1-methyl ester.

The compounds are metabolites of Antrodin C in rats, and the Antrodin C is isolated from the myvelium *Antrodia cinnamomea*.

The present invention provides a composition comprising a compound having the formula

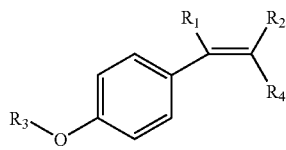

wherein $R_1$ is $C_{1-10}$ carboxylic acid or $C_{1-10}$ ester; $R_2$ is $C_{1-10}$ carboxylic acid or $C_{1-10}$ ester; $R_3$ is H, $C_{1-10}$ alkyl, $C_{2-10}$ alkenyl or $C_{2-10}$ alkynyl; and $R_4$ is H, $C_{1-10}$ alkyl, $C_{2-10}$ alkenyl or $C_{2-10}$ alkynyl.

In the preferred embodiment, the compound is (2Z)-2-isobutyl-3-{4-[(3-methylbut-2-en-1-yl)oxy]phenyl}but-2-enedioic acid, (2Z)-2-isobutyl-3-{4-[(3-methylbut-2-en-1-yl)oxy]phenyl}but-2-enedioic acid 4-methyl ester or (2Z)-2-isobutyl-3-{4-[(3-methylbut-2-en-1-yl)oxy]phenyl}but-2-enedioic acid 1-methyl ester.

The present invention provides the compounds have possessing antioxidation, antimicrobial, antibacterial actions, AChE inhibitory activity, antispasmodic or vasorelaxant activities.

The compound of the invention can decrease systolic blood pressure or increase high density lipoprotein. In addition, the same compound has central cholinergic agonism, hepatoprotection, anti-inflammation or anti-tumor activity. Especially, the compound of the invention can inhibit tumor from the cells or tissues selected from the group consisting of liver, lung, intestine, bone, blood, lymph and breast. The subject accepting the mixture of the invention includes but is not limited to human, mammal, mouse, rat, horse, pig, chicken, duck, dog and cat.

The present invention also provides a composition, which comprises the compound of the invention. The composition of the invention can decrease systolic blood pressure or increase high density lipoprotein. In addition, the composition of the invention has central cholinergic agonism, hepatoprotection, anti-inflammation or anti-tumor activity. Especially, the compound of the invention can inhibit tumor from the cells or tissues selected from the group consisting of liver, lung, intestine, bone, blood, lymph and breast. The subject accepting the mixture of the invention includes but is not limited to human, mammal, mouse, rat, horse, pig, chicken, duck, dog and cat.

EXAMPLE

Chemicals and Reagents

General anaerobic medium (GAM) broth was purchased from Nissui Co. (Tokyo, Japan). Liquid chromatographic grade solvents, trietylamine, 4-dimethylaminopyridine (4-DMAP), silica gel BW-820MH (Fuji Silysia), ODS DM 1020T (Fuji Silysia) for open column chromatography, Merck precoated Silica gel $60F_{254}$ (0.25 mm) and Merck RP-$18F_{254}$ (0.25 mm) for TLC analysis were obtained from Wako Pure Chemical Industries Ltd. (Osaka, Japan).

Instruments

Compounds were analyzed by $^1$H- and $^{13}$C-NMR and 2D NMR using a Unity Plus 500 (varian) NMR spectrometer with tetramethylsilane as an internal standard, and chemical shifts are shown as δ values. Intestinal bacteria were anaerobically incubated using an EAN-140 (Tabai Co., Osaka, Japan). The HPLC instrument was an Agilent 1100 system (Agilent Technologies, Waldbronn, Germany) comprising an Agilent 1100 series binary pump with a photodiode array detector (PAD) and a series 7725i injector with a 20 μl loop. Data were acquired and integrated using a ChemStation. The HPLC system was connected to an Esquire $3000^{plus}$ mass spectrometer (Bruker Daltonik GmbH, Bremen, Germany) equipped with an ESI source. All LC/MS-MS data were acquired using Esquire Control software and analyzed using software from by Bruker Daltonics.

Example 1

Synthesis of M1-M3

Antrodin C (50 mg) was dissolved in 5 ml water, and 1N KOH (0.5 ml) was added stirring for 5 min. 1N HCl was used to adjust PH to 8. After filtration, the solution kept under room temperature overnight. After filtration again, the supernatant was lyophilized, and reconstitute by some MeOH, and then filtered and evaporated in vacuo., yield of M1 was 13 mg (26%).

The $^1$H and $^{13}$C-NMR spectra of M1 (Table 1) was very similar to those of Antrodin C and showed the presence of isobutyl moiety, a 3-methyl-2-butenyloxy moiety, and a para-substituted benzene ring, which supported by $^1$H-$^1$H COSY, HMQC experiments. But carbonyl carbon (δ 178.9:1), methylene carbon (δ 39.7:1'), proton (δ 1.87:1') and methyne proton (δ 1.56:2') of isobutyl moiety, benzene carbon conjugated olefine (δ 131.6:1") and benzene proton next to that (δ 7.11: 2", 6") were different from those of Antrodin C, these all the carbon of M1 were downfield shifted than those of Antrodin C and these all the proton of M1 were upfield shifted than those of Antrodin C. In the HMBC experiments, long-range correlations were observed as shown in FIG. 1(*a*). We decided that Olefine coupling (2-C and 3-C) of M1 is Z because NOE was observed between 1'-H and 3'4'-H or 6"-H in the NOESY spectrum of M1 (FIG. 1(*b*)). According to these results, M1 was defined as (2Z)-2-isobutyl-3-{4-[(3-methylbut-2-en-1-yl)oxy]-phenyl}but-2-enedioic acid. Anhydride M4 (Antrodin A) and dicarboxylic acid M1 were converted each other by acid and base condition.

Figure 2:
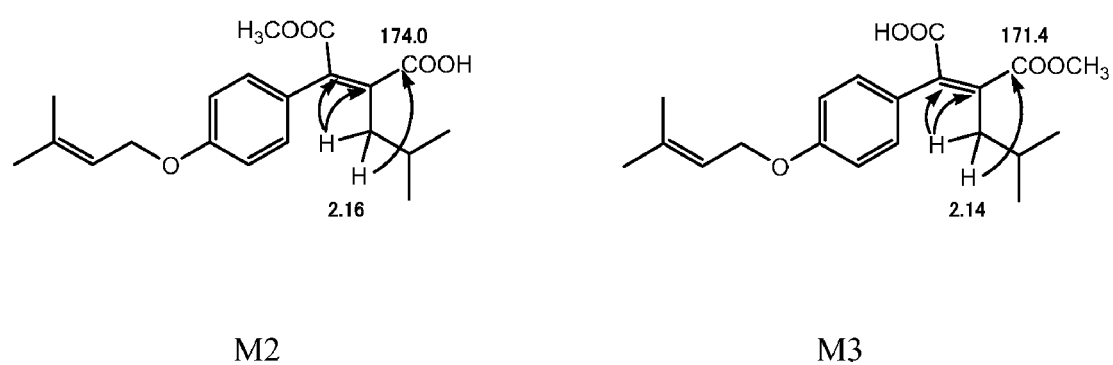
FIG. 2 HMBC Correlations of M2 and M3.

Antrodin A (500 mg) was dissolved in 1 ml MeOH, and trietylamine (0.2 ml, 1.6 mmol) and 4-dimethylaminopyridine (4-DMAP, 13.4 mg, 0.11 mmol) were added to the solution stirring for 20 h at 25° C. And then the mixture was chromatographed by a open ODS column eluting with methanol and water (30:70→100:0), the fraction containing M2 and M3 were evaporated in vacuo, and then analyzed by NMR and LC/MS. The data of $^1$H-NMR and $^{13}$C-NMR of M1-M3 were showed in Table 1, 2. The $^1$H and $^{13}$C-NMR spectra of M2 and M3 were also similar to those of M1 except for methoxy groups and showed the presence of isobutyl moiety, a 3-methyl-2-butenyloxy moiety, and a para-substituted benzene ring. In the HMBC experiments, methylene proton of isobutyl moiety (δ 2.16:1') and carbonyl carbon (δ 174.0:1) of M2 showed long-range correlation, and methylene proton of isobutyl moiety (δ 2.14:1') and carbonyl carbon (δ 171.4:1) of M3 showed long-range correlation (FIG. 2). The structure of M2 and M3 were defined as (2Z)-2-isobutyl-3-{4-[(3-methylbut-2-en-1-yl)oxy]phenyl}but-2-enedioic acid 4-ester and (2Z)-2-isobutyl-3-{4-[(3-methylbut-2-en-1-yl)oxy]phenyl}but-2-enedioic acid 1-methyl ester, respectively.

TABLE 1

¹H-NMR Spectral Data of M1 (D₂O), M2 and M3 (CD₃OD) (δ ppm, J = Hz)

| | M1 | M2 | M3 |
|---|---|---|---|
| 1' | 1.87 (2H, d, J = 6.5) | 2.16 (2H, d, J = 7.0) | 2.14 (2H, d, J = 7.0) |
| 2' | 1.56 (1H, m) | 1.69 (1H, m) | 1.69 (1H, m) |
| 3', 4' | 0.72 (6H, d, J = 6.5) | 0.81 (6H, d, J = 7.0) | 0.80 (6H, d, J = 6.5) |
| 2", 6" | 7.11 (2H, d, J = 8.5) | 7.14 (2H, d, J = 9.0) | 7.20 (2H, d, J = 9.0) |
| 3", 5" | 6.88 (2H, d, J = 8.5) | 6.91 (2H, d, J = 9.0) | 6.91 (2H, d, J = 9.0) |
| 1''' | 4.50 (2H, d, J = 6.5) | 4.54 (2H, d, J = 6.5) | 4.54 (2H, d, J = 6.5) |
| 2''' | 5.41 (1H, brs) | 5.46 (1H, m) | 5.46 (1H, m) |
| 4''' | 1.68 (3H, s) | 1.77 (3H, s) | 1.77 (3H, s) |
| 5''' | 1.64 (3H, s) | 1.75 (3H, s) | 1.75 (3H, s) |
| —OMe | — | 3.82 (3H, s) | 3.72 (3H, s) |

TABLE 2

¹³C-NMR Spectral Data of M1 (D₂O), M2 and M3 (CD₃OD) (δ ppm)

| | M1 | M2 | M3 |
|---|---|---|---|
| 1 | 178.9 | 174.0* | 171.4* |
| 2 | 140.3 | 144.0 | 134.3 |
| 3 | 137.5 | 136.3 | 145.4 |
| 4 | 166.1 | * | * |
| 1' | 39.7 | 40.0 | 40.0 |
| 2' | 27.2 | 29.0 | 29.0 |
| 3', 4' | 22.2 | 22.8 | 22.8 |
| 1" | 131.6 | 128.5 | 128.5 |
| 2", 6" | 130.5 | 131.4 | 131.0 |
| 3", 5" | 114.8 | 115.5 | 115.5 |
| 4" | 157.0 | 160.0 | 160.0 |
| 1''' | 65.3 | 65.9 | 65.9 |
| 2''' | 118.4 | 121.1 | 121.1 |
| 3''' | 141.6 | 138.7 | 138.7 |
| 4''' | 25.1 | 25.9 | 25.9 |
| 5''' | 17.3 | 18.2 | 18.2 |
| —OMe | — | ** | ** |

Example 2

Treatment of Animals

Male Wistar rats (9 weeks old) purchased from SLC Co. (Hamamastu, Japan), were fed with standard laboratory chow for one week, fasted overnight and given free access to water before drug administration. Urine and feces samples were collected while the rats remained isolated in metabolic cages. The animals were light anesthetized with diethyl ether during surgical procedures. Bile samples (n=5) was collected by cannulating a polyethylene tube (PE-10) into the rat bile duct at intervals of 0, 0.25, 0.5, 1, 2, 4, 8, 12, 24, 36 and 48 h after oral (50 mg/kg) and intravenous (10 mg/kg) administration of Antrodin C. The blood sample was collected from the inferior vena cava using a heparinized injector when the abdomen was exposed by a midline abdominal incision after administration. The blood samples were centrifuged at 8000×g for 15 min to separate the plasma, and then all samples were stored at −20° C. for later analysis.

Sample Preparation for Analysis

Thawed urine and bile samples (0.5 ml) dissolved in 3 volumes of acetonitrile, and then centrifuged at 8000×g for 15 min. The supernatant was passed through a 0.45 µm Millipore syringe filter (Nihon Millipore, Tokyo, Japan) for LC/MS-MS analysis. Plasma samples were passed through Solid Phase Extraction cartridges (Waters Co., Milford, U.S.A.) that had been washed with 3 ml of acetonitrile and equilibrated with 6 ml of water. The constituents were eluted with 2-3 ml of acetonitrile from the cartridge, then the eluate was evaporated under a stream of nitrogen at 35° C. to leave a residue that was dissolved in 100 µl of acetonitrile for LC/MS-MS analysis. The bile samples for pharmacokinetic study, which containing M2, M3 and M4 were diluted by same volume water, and then incubated in 37° C. bath for 12 h, the M2-M4 would thoroughly converted to M1. After treating the bile sample as described above, the amount of M1 was calculated by PAD-HPLC.

Identification of Metabolites in Rat feces, Bile and Plasma

Figure 3:
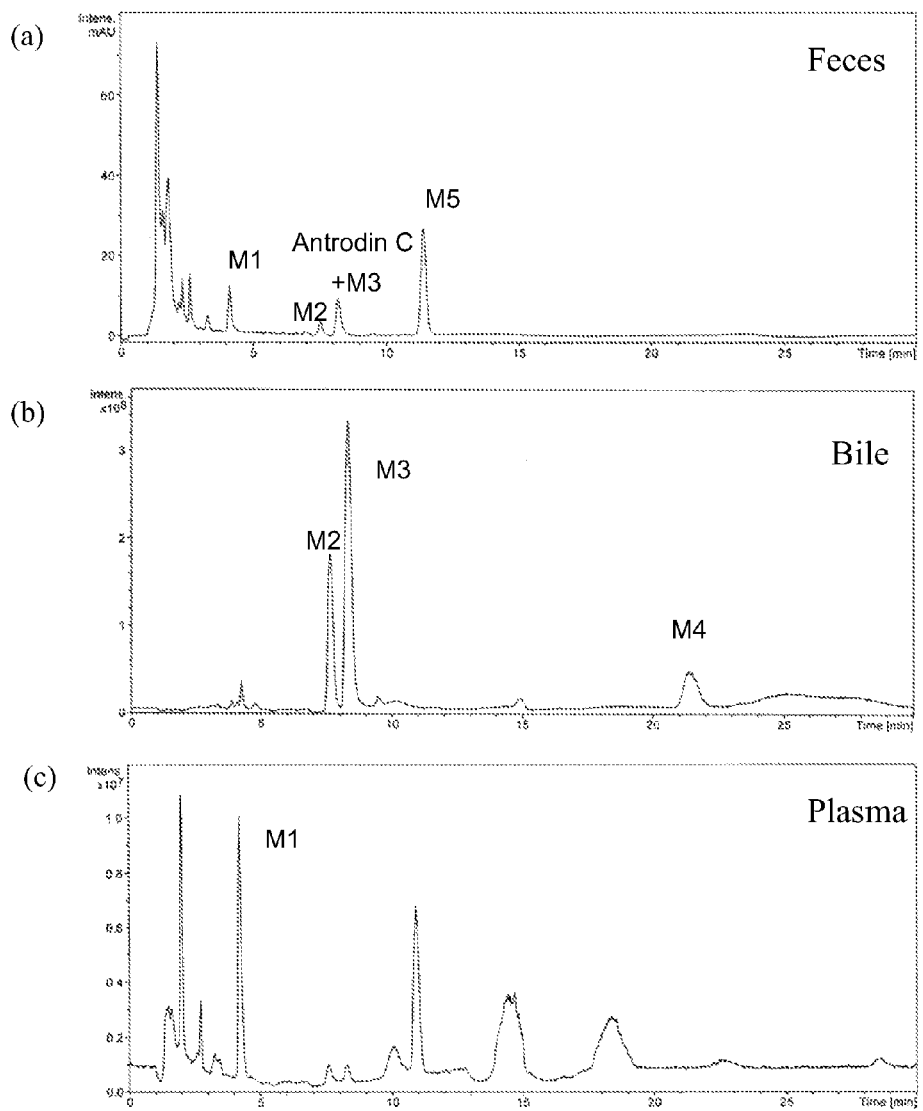
FIG. 3 TIC of feces (a), bile (b) and plasma (c) sample after oral administration of Antrodin C at the dose of 50 mg/kg.
Figure 4:
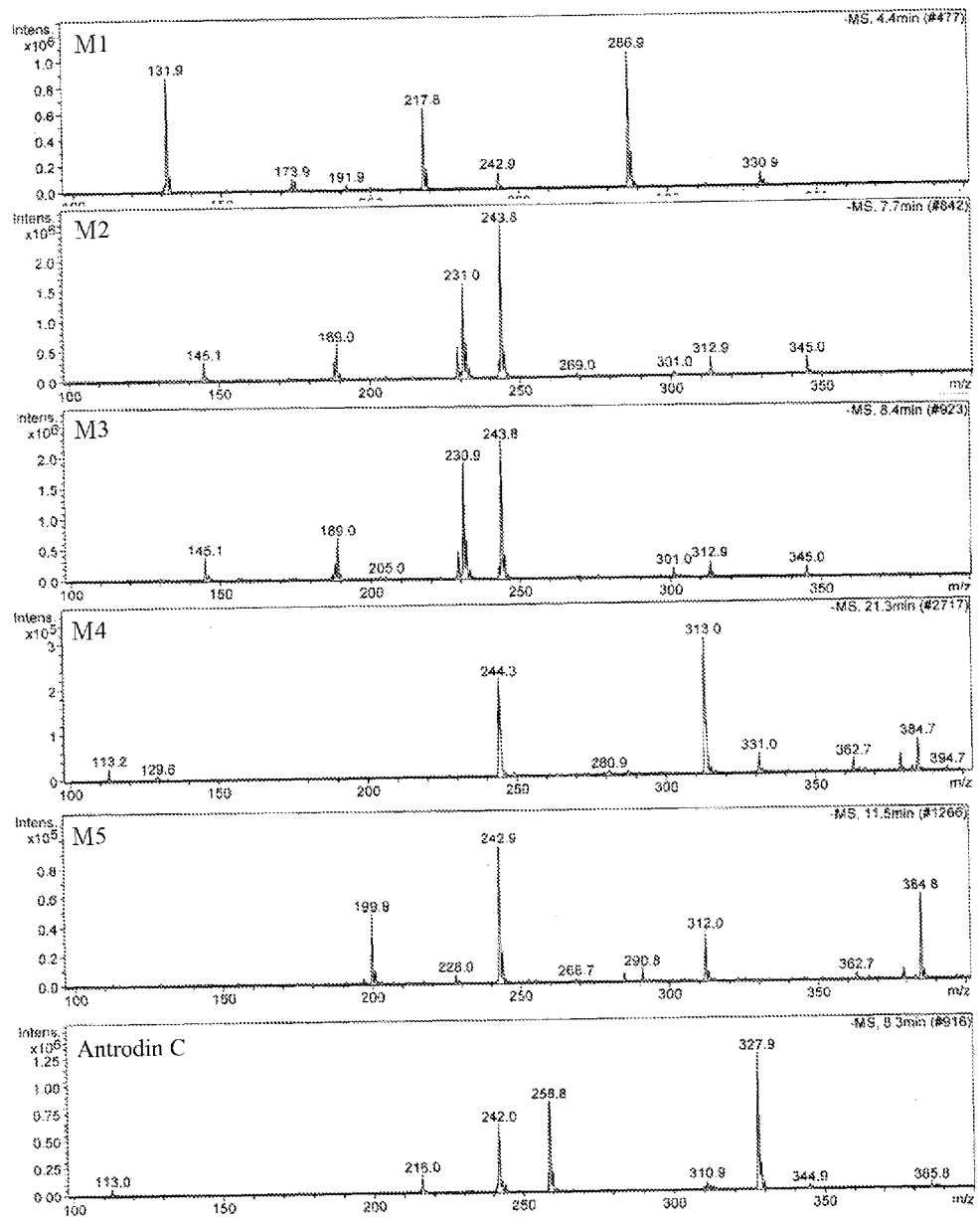
FIG. 4 MS spectra (negative mode) of M1-M5 and Antrodin C in the rat feces, bile and plasma samples.
Figure 5:
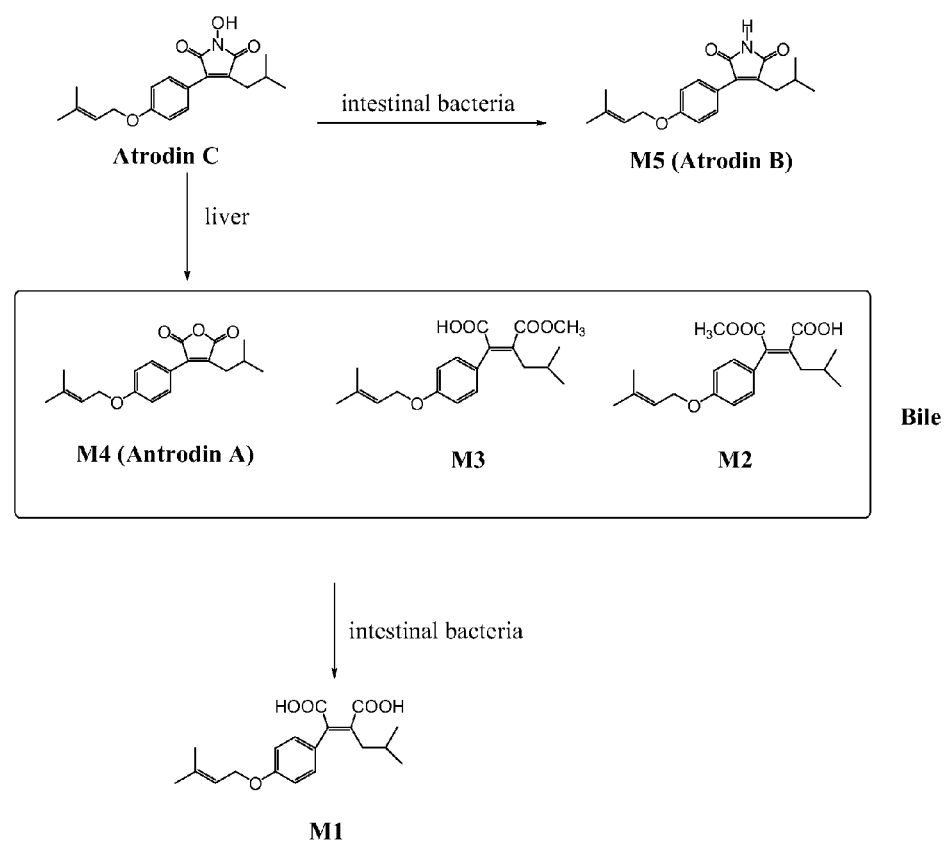
FIG. 5 The structures of Antrodin C and its metabolites.

The metabolites in feces, bile and plasma were analyzed by LC/MS-MS. The LC/MS-MS equipment comprised a column containing TSK gel ODS-80 Ts (particle size, 5 µm; 4.6×150 mm i.d., Tosoh Co., Tokyo, Japan). Samples were eluted through the column with 0.1% AcOH and acetonitrile (35:65) at a flow rate of 1 ml/min at 30° C. The standard negative ion mode was selected under the following conditions: full scan range, 50-800 m/z; scan resolution, 13000 m/z/sec; nebulizer, 50.0 psi; dry gas, 10.0 l/min; dry temperature, 360° C. Full scanning in the region of m/z 50 to 600 assigned several peaks to Antrodin C and the metabolites in the TLC when compared with those of blank samples (FIG. 3). The MS spectra revealed intense ion peaks at m/z 331, 345, 345, 313, 312 and 328 [M-H]⁻ as M1, M2, M3, M4, M5 and Antrodin C, respectively (FIG. 4, Table 3). In the feces, metabolites were M1-M3, M5 with original Antrodin C; in the bile were M2-4; and in the plasma were M1 with another unknown peak. There was neither metabolite nor Antrodin C in the urine sample. Comparing to standard materials and synthesized compounds, the peak in the MS profile at m/z 328 [M-H]⁻ with retention time ($t_R$)=8.2 min was derived from Antrodin C (MW 329), and M1 (m/z 331 [M-H]⁻, $t_R$=4.4 min) was dicarboxylic acid by hydrolysis of Antrodin C; M2 and M3 (m/z 345 [M-H]⁻, $t_R$=7.7 and 8.4 min), which were 14 larger than those of M1, were two kinds of monomethyl esters of M1; M4 (m/z 313 [M-H]⁻, $t_R$=21.6 min) was Antrodin A and M5 (m/z 312 [M-H]⁻, $t_R$=11.5 min) was Antrodin B. The structures of Antrodin C and its metabolites were shown in FIG. 5.

TABLE 3

Retention time ($t_R$) and MS spectra of Antrodin C and its metabolites

| | $t_R$ | MS spectra (Negative mode) |
|---|---|---|
| Antrodin C | 8.2 | 328, 259, 242, 216 |
| M1 | 4.4 | 331, 287, 218, 132 |
| M2, M3 | 7.7, 8.4 | 345, 313, 244, 232, 189 |
| M4 | 21.6 | 313, 244 |
| M5 | 11.5 | 312, 243, 200 |
| Unknown metabolite | 10.8 | 319, 301, 257, 179, 163, 135 |

Metabolism of Antrodin C and Metabolites by Intestinal Bacteria In Vitro

Mixtures of rat (RIB) or human (HIB) intestinal bacteria (5 g each) prepared as described (Xie L H, et al. 2003 Biol Pharm Bull 51: 378-384), together with Antrodin C (5 mg) dissolved in Tween 20 (0.5 ml), M1 (5 mg) dissolved in water (1.0 ml) or rat bile samples (10 ml) with metabolites M2-M4, which were collected after oral administration of Antrodin C, were added to GAM broth (50 ml), and anaerobically incubated at 37° C. for 3 d. The incubation mixture was extracted with 3 volumes of acetonitrile, and then passed through a 0.45 µm filter. Then, Antrodin C was converted to M5 (Antrodin B). Moreover, the metabolites (M2-M4) in bile samples, which were collected after oral administration of Antrodin C in rats, could absolutely transferred to M1 after 30 min incubation. Whereas M1 was not metabolized by intestinal bacteria flora, although prolonged the incubation time to 3 d.

Validation of M1 by PAD-HPLC

Linearity: M1 was dissolved in rat blank bile to prepare seven dilutions of standard solutions. Response linearity was determined for the seven concentrations after three injections for each level. The limit of detection (LOD) of the method for each constituent was established when the signal to noise ratio (S/N) was 5.

Accuracy: Intra- and inter-assay variability was determined by analyzing high, medium and low standard concentrations of rat bile five times on the same day and continuously for 5 d, respectively.

Recovery: Two standard concentrations were mixed with rat bile samples after the oral administration of Antrodin C with a known amount of M1, and recovery rates of the added amounts were calculated.

Stability: Three concentrations of bile samples that had been prepared for PAD-HPLC analysis were placed at room temperature for 12 h, or in a refrigerator at 4° C. for 1, 3 and 5 d. The average peak areas of constituents in the samples and relative standard deviation (RSD) were calculated.

Validation of PAD-HPLC Quantitation

The regression equation of M1 in rat bile sample was $Y=610.22X-3.94$; $\gamma=0.9998$; and the linearity range was 0.05-2.0 μg/ml. Intra-day and inter-day (n=5) variations of M1 in rat bile samples were shown in Table 4. The CV did not exceed 6%, and the accuracy rates were all within 85-110%. CV values of recovery rates were shown in Table 5, which were less than 10% at low and high concentrations with recovery rates of 93.4 and 99.6%. The stability test showed that relative standard deviation remained within 5% under all the conditions; therefore, the samples were stable during the test. Thus, the accuracy, recovery, and stability tests met the criteria for quantitative determinations in bile samples.

TABLE 4

Intraday and Interday (n = 5) Variations of M1 in Rat Bile

|  | Added (μg) | Found (μg) | Accuracy (%) | CV (%) |
|---|---|---|---|---|
| Intraday | 0.05 | 0.0456 ± 0.0018 | 91.2 | 3.9 |
|  | 0.5 | 0.533 ± 0.008 | 106.6 | 1.5 |
|  | 2.0 | 1.99 ± 0.04 | 99.5 | 2.0 |
| Interday | 0.05 | 0.0438 ± 0.0026 | 87.6 | 5.9 |
|  | 0.5 | 0.443 ± 0.009 | 88.6 | 2.0 |
|  | 2.0 | 1.98 ± 0.06 | 99.0 | 3.0 |

TABLE 5

Recovery of M1 in Rat Bile

| Added (μg) | Found (μg) | Recovery (%) | CV (%) |
|---|---|---|---|
| 0.05 | 0.0467 ± 0.0045 | 93.4 | 9.6 |
| 0.5 | 0.498 ± 0.020 | 99.6 | 4.0 |

Pharmacokinetics of M1 in Rat Bile

The concentration-time data in rat bile (n=5) were computer fitted using a program of Pharmacokineitics 3p97 edited by the Mathematics Pharmacological Committee, Chinese Pharmacological Society. The following pharmacokinetic parameters were obtained: half-time of absorption phase ($t_{1/2\ (K\alpha)}$) and half-time of elimination phase ($t_{1/2\ (K\beta)}$) in the bile samples after oral administration of Antrodin C at the dose of 50 mg/kg. The area under the concentration-time curve ($AUC_{(i.v.)}$ and $AUC_{(p.o.)}$) was calculated by the statistical moment method of non-compartmental pharmacokinetic analysis. And then clearance ($Cl_{m,\ b}$) and absolute bioavailability ($F_{m,\ b}$) were calculated by the equations as following: $Cl_{m,\ b}$ (ml/h·kg)=$Dose_{(i.v.)}/AUC_{(i.v.)}$ and $F_{m,\ b}$ (%)=$AUC_{(p.o.)} \cdot Dose_{(i.v.)}/[AUC_{(i.v.)} \cdot Dose_{(p.o.)}]$. Data were expressed mean and standard deviation (S.D.) for each group.

Figure 6:
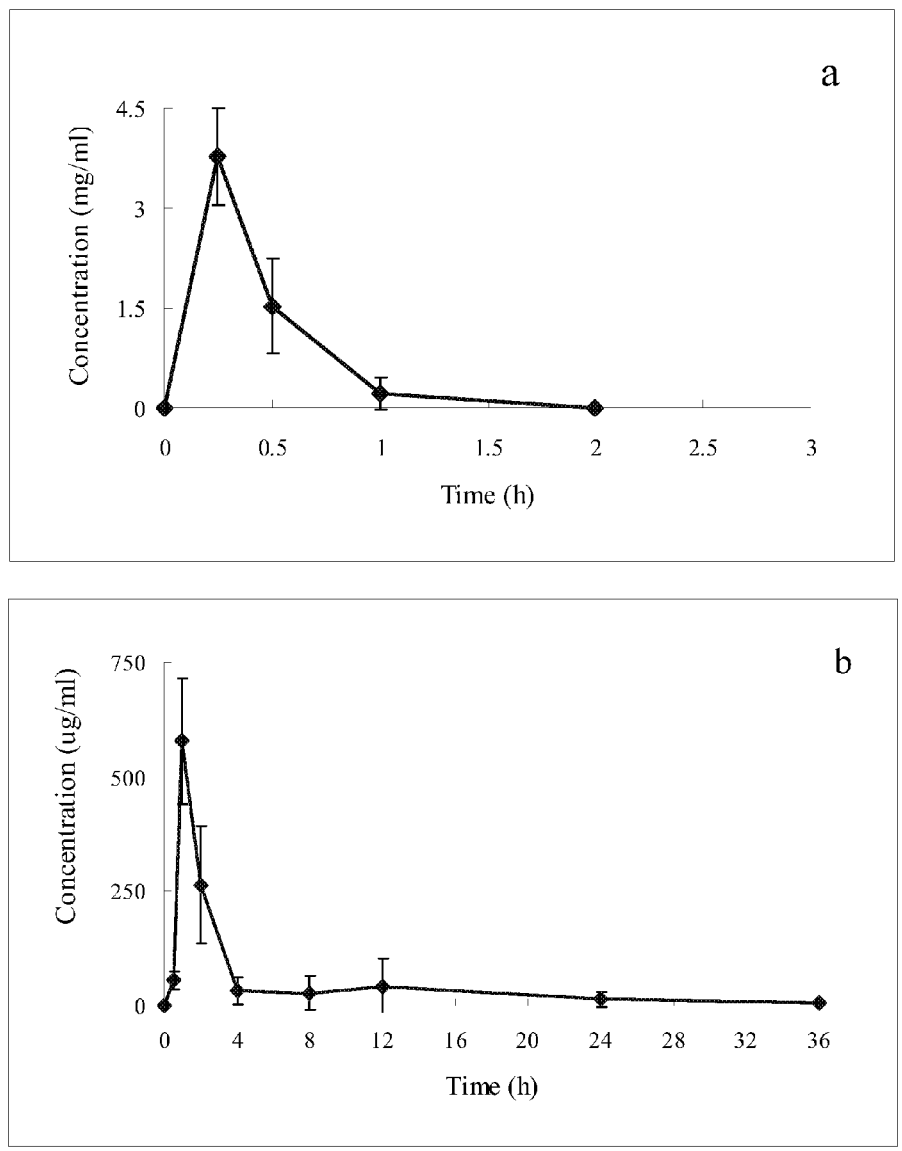
FIG. 6 Concentration-time curve of M1 in bile samples after I.V. Antrocin C at the dose of 10 mg/kg (a) and P.O. 50 mg/kg (b).

The concentrations of M1 in bile samples were calculated after P.O. administration of 50 mg/kg and I.V. 10 mg/kg of Antrodin C. The concentration-time curves of M1 were shown in FIG. 6. The pharmacokinetic parameters were shown in Table 6. After oral administration, $t_{1/2\ (k\alpha)}$ and $t_{1/2\ (k\beta)}$ were 0.95 h and 12.64 h, respectively. $AUC_{0-lim}$ were 1.61 (P.O.) and 1.68 h mg/ml (I.V.), $Cl_{m.b.}$ was 5.96 ml/h·kg and $F_{m.b.}$ was 19.43(%). Accumulated excretion ratio of Antrodin C were 5.46±1.62% (P.O.) and 56.85±13.40 (I.V.). Therefore, Antrodin C was very quickly not only absorbed from gastrointestine, but also metabolized in the liver. The mainly excretion was bile-feces pathway in rats.

TABLE 6

Pharmacokinetic parameters of M1 in rat bile samples after P.O. and I.V. of Antrodin C

| P.O. (50 mg/kg) | | | I.V. (10 mg/kg) | | |
|---|---|---|---|---|---|
| | | | | $Cl_{m.b.}$ | |
| $t_{1/2\ (k\alpha)}$ (h) | $t_{1/2\ (k\beta)}$ (h) | $AUC_{0-lim}$ (h mg/ml) | $AUC_{0-lim}$ (h mg/ml) | (ml/ h kg) | $F_{m.b.}$ (%) |
| 0.95 ± 0.07 | 12.64 ± 2.24 | 1.61 ± 0.58 | 1.68 ± 0.31 | 5.96 | 19.43 |

Example 3

Figure 7:
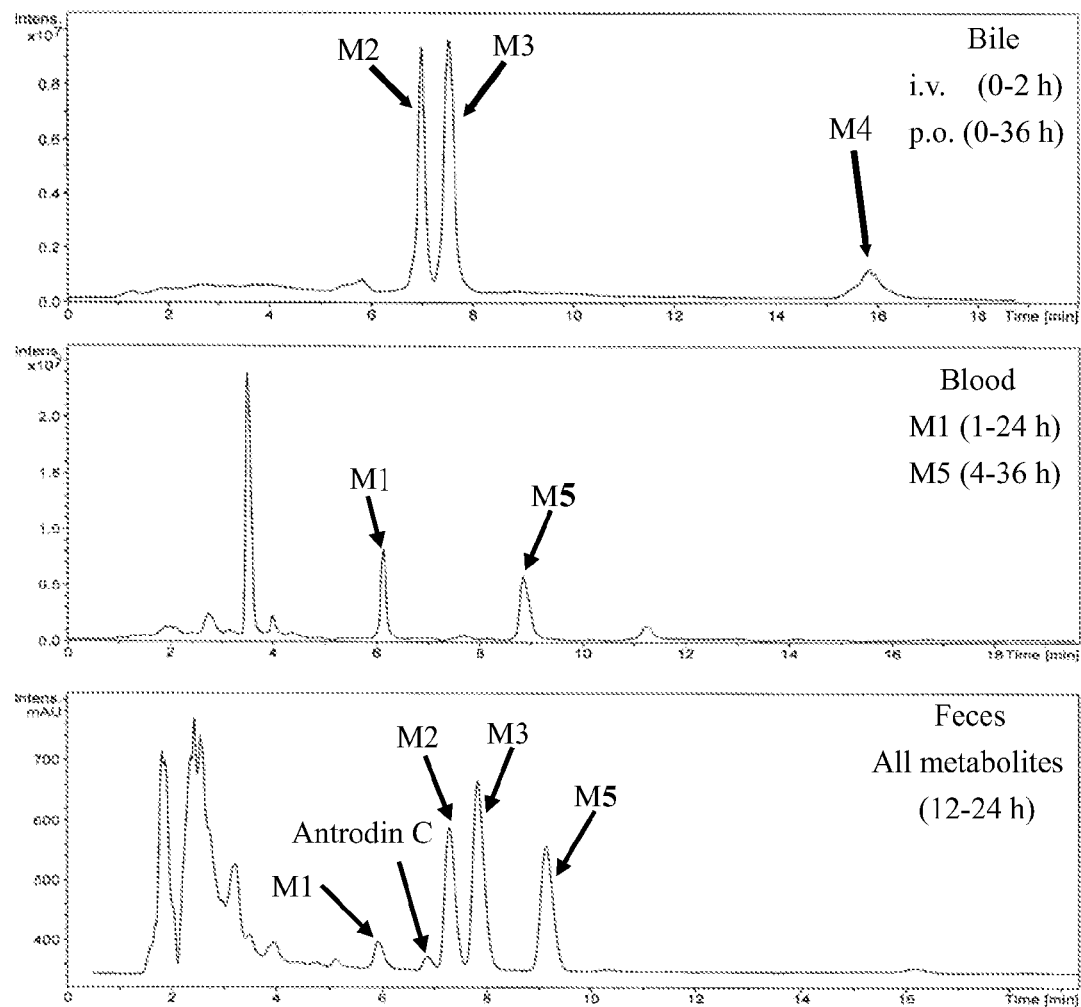
FIG. 7 The TIC of Bile and Plasma and the UV Spectra of Faeces after Administration of Antrodin C in Rats
FIG. 8 The UV spectra of the blank plasma samples and the plasma samples after i.v. of M1
Figure 8:
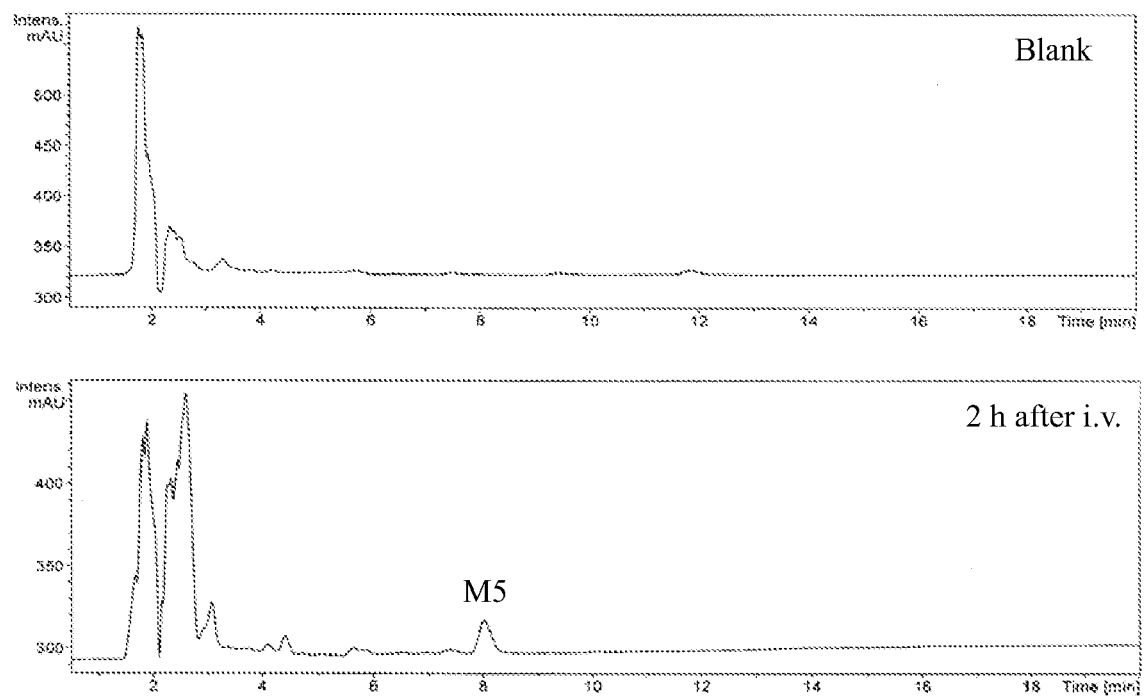

Repeat example 2, results are shown in FIG. 7 and FIG. 8

What is claimed is:

1. An isolated compound having the formula

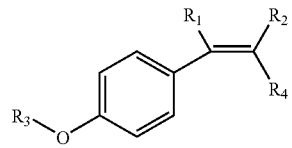

wherein
  $R_1$ is $C_{1-10}$ carboxylic acid or $C_{1-10}$ ester;
  $R_2$ is $C_{1-10}$ carboxylic acid or $C_{1-10}$ ester;
  $R_3$ is H, $C_{1-10}$ alkyl, $C_{2-10}$ alkenyl or $C_{2-10}$ alkynyl; and
  $R_4$ is H, $C_{2-10}$ alkyl, $C_{2-10}$ alkenyl or, C2-10 alkynyl.

2. The isolated compound of claim 1, wherein $R_1$ or $R_2$ is $C_{1-6}$ carboxylic acid.

3. The isolated compound of claim 1, wherein $R_1$ or $R_2$ is COOH.

4. The isolated compound of claim 1, wherein $R_3$ is $C_{1-6}$ alkyl.

5. The isolated compound of claim 1, wherein $R_4$ is isobutyl.

6. The isolated compound of claim 1, which is (2Z)-2-isobutyl-3-{4-[(3-methylbut-2-en-1-yl)oxy]phenyl}but-2-enedioic acid, (2Z)-2-isobutyl-3-{4-[(3-methylbut-2-en-1-yl)oxy]phenyl}but-2-enedioic acid 4-methyl ester or (2Z)-2-isobutyl-3-{4-[(3-methylbut-2-en-1-yl)oxy]phenyl}but-2-enedioic acid 1-methyl easter.

7. The isolated compound of claim 6, wherein the compound is metabolites of Antrodin C in rats.

8. A composition comprising an isolated compound having the formula

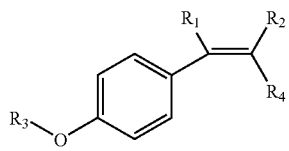

wherein
$R_1$ is $C_{1-10}$ carboxylic acid or $C_{1-10}$ ester;
$R_2$ is $C_{1-10}$ carboxylic acid or $C_{1-10}$ ester;
$R_3$ is H, $C_{1-10}$ alkyl, $C_{2-10}$ alkenyl or $C_{2-10}$ alkynyl; and
$R_4$ is H, $C_{2-10}$ alkenyl, $C_{2-10}$ alkynyl or isobutyl.

9. The composition of claim 8, wherein the isolated compound is (2Z)-2-isobutyl-3-{4-[(3-methylbut-2-en-1-yl)oxy]phenyl}but-2-enedioic acid, (2Z)-2-isobutyl-3-{4-[(3-methylbut-2-en-1-yl)oxy]phenyl}but-2-enedioic acid 4-methyl ester or (2Z)-2-isobutyl-3-{4-[(3-methylbut-2-en-1-yl)oxy]phenyl}but-2-enedioic acid 1-methyl easter.

* * * * *